(12) United States Patent
Riggins et al.

(10) Patent No.: US 8,394,580 B2
(45) Date of Patent: Mar. 12, 2013

(54) PROTEIN MARKERS FOR THE DETECTION OF THYROID CANCER METASTASIS

(75) Inventors: Gregory Riggins, Baltimore, MD (US); Janete Cerutti, Sao Paolo (BR)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 12/222,876

(22) Filed: Aug. 18, 2008

(65) Prior Publication Data

US 2009/0068171 A1    Mar. 12, 2009

Related U.S. Application Data

(60) Provisional application No. 60/965,208, filed on Aug. 17, 2007.

(51) Int. Cl.
| | |
|---|---|
| *C12Q 1/00* | (2006.01) |
| *C12Q 1/68* | (2006.01) |
| *G01N 33/48* | (2006.01) |
| *G01N 33/53* | (2006.01) |
| *G01N 33/567* | (2006.01) |
| *G01N 33/574* | (2006.01) |
| *G01N 1/00* | (2006.01) |

(52) U.S. Cl. ................. 435/4; 435/6; 435/7.1; 435/7.21; 435/7.23; 436/63; 436/64; 436/174

(58) Field of Classification Search ......................... None
See application file for complete search history.

(56) References Cited

U.S. PATENT DOCUMENTS

2007/0065833 A1 *   3/2007   Gupta ................................ 435/6
2008/0118518 A1 *   5/2008   Cirrito et al. ................ 424/155.1

OTHER PUBLICATIONS

Cerutti et al. Molecular profiling of matched samples identifies biomarkers of papillary thyroid carcinoma lymph node mestastasis. Cancer Research 67(16): 7885-7892.*
Konishi et al. Overexpresion of leucocyte common antigen (LAR) P-subunit in thyroid carcinomas. British Journal of Cancer 88: 1223-1228, 2003.*
Jang et al. An examination of the effects of hypoxia, acidosis, and glucose starvation on the expression of metastasis-associated genes in murine tumor cells. Clinical and Experimental Metastasis 15: 469-483, 1997.*
Cerutti et al. (Cancer Research 67(16): 7885-7892, Aug. 15, 2007).*

* cited by examiner

*Primary Examiner* — Alana Harris Dent
(74) *Attorney, Agent, or Firm* — Johns Hopkins Technology Transfer

(57) ABSTRACT

This invention relates, e.g., to a method for detecting the presence of lymph node metastases in a subject having papillary thyroid carcinoma (PTC), comprising measuring in a sample from the subject the amount of expression (e.g., the amount of protein, or the amount of mRNA encoding the protein) of one or more of the following proteins: (a) LIMD2, and/or (b) PTPRC, and/or (c) LTB, and/or (d) CD48, and/or (e) ABCC3, wherein a significant amount of over-expression of one or more of protein(s) (a)-(e), compared to the baseline value, indicates that lymph node metastases are likely to be present in the subject.

18 Claims, 2 Drawing Sheets

SEQUENCE LISTING

<160> NUMBER OF SEQ ID NOS: 14

<210> SEQ ID NO 1
<211> LENGTH: 10
<212> TYPE: DNA
<213> ORGANISM: Homo sapiens

<400> SEQUENCE: 1
gtcaacagta                                                          10

<210> SEQ ID NO 2
<211> LENGTH: 10
<212> TYPE: DNA
<213> ORGANISM: Homo sapiens

<400> SEQUENCE: 2
gcagtgggaa                                                          10

<210> SEQ ID NO 3
<211> LENGTH: 10
<212> TYPE: DNA
<213> ORGANISM: Homo sapiens

<400> SEQUENCE: 3
gtagcgcctc                                                          10

<210> SEQ ID NO 4
<211> LENGTH: 10
<212> TYPE: DNA
<213> ORGANISM: Homo sapiens

<400> SEQUENCE: 4
ttaactgtgt                                                          10

<210> SEQ ID NO 5
<211> LENGTH: 10
<212> TYPE: DNA
<213> ORGANISM: Homo sapiens

<400> SEQUENCE: 5
cttttttccc                                                          10

-continued

```
<210> SEQ ID NO 6
<211> LENGTH: 10
<212> TYPE: DNA
<213> ORGANISM: Homo sapiens

<400> SEQUENCE: 6
ttaaatccca                                                           10

<210> SEQ ID NO 7
<211> LENGTH: 10
<212> TYPE: DNA
<213> ORGANISM: Homo sapiens

<400> SEQUENCE: 7
aaagcaaaaa                                                           10

<210> SEQ ID NO 8
<211> LENGTH: 10
<212> TYPE: DNA
<213> ORGANISM: Homo sapiens

<400> SEQUENCE: 8
tttcaataga                                                           10

<210> SEQ ID NO 9
<211> LENGTH: 10
<212> TYPE: DNA
<213> ORGANISM: Homo sapiens

<400> SEQUENCE: 9
gaggccatcc                                                           10

<210> SEQ ID NO 10
<211> LENGTH: 10
<212> TYPE: DNA
<213> ORGANISM: Homo sapiens

<400> SEQUENCE: 10
caattaaaat                                                           10

<210> SEQ ID NO 11
<211> LENGTH: 10
<212> TYPE: DNA
<213> ORGANISM: Homo sapiens

<400> SEQUENCE: 11
caggccccac                                                           10

<210> SEQ ID NO 12
<211> LENGTH: 10
<212> TYPE: DNA
<213> ORGANISM: Homo sapiens

<400> SEQUENCE: 12
gatgaataaa                                                           10

<210> SEQ ID NO 13
<211> LENGTH: 10
<212> TYPE: DNA
<213> ORGANISM: Homo sapiens

<400> SEQUENCE: 13
cggtgaagca                                                           10
```

```
<210> SEQ ID NO 14
<211> LENGTH: 10
<212> TYPE: DNA
<213> ORGANISM: Homo sapiens

<400> SEQUENCE: 14
atgctaagag                                                          10
```

PROTEIN MARKERS FOR THE DETECTION OF THYROID CANCER METASTASIS

This application claims the benefit of the filing date of provisional patent application 60/965,208, filed Aug. 17, 2007, which is incorporated by reference in its entirety herein.

This application was made with U.S. government support (NIH Grant CA113461). The U.S. government thus has certain rights in the invention.

This application contains a sequence listing. It has been submitted electronically via EFS-Web as an ASCII text file entitled "P10120-02_ST25.txt." The sequence listing is 4,096 bytes in size, and was created on Jul. 13, 2012. It is hereby incorporated by reference in its entirety.

BACKGROUND INFORMATION

Papillary thyroid carcinoma (PTC) is the most common thyroid cancer, accounting for about 80% of all thyroid cancers. Although PTCs are usually curable with standard surgical and adjuvant radioiodine treatment, neck lymph node metastases are found in 30-65% of cases at initial diagnosis (1-3). Lymph nodes are the most frequent site of PTC metastasis and, if found, predict recurrence and poor survival (20). It is the presence of these and more distant metastases that are generally are the cause of death from the cancer, rather than the invasion of the primary tumors, themselves. Because lymph node metastases are often difficult to detect by eye, such metastases can be missed by current technologies, particularly at early stages of metastasis. Furthermore, lymph node metastases have been identified in the absence of a clinically detectable primary tumor. It would be beneficial to have an earlier and more accurate detection of lymph node metastases, so that patients having such metastases could be treated aggressively, whereas patients not exhibiting such metastases could be spared the adverse effects of such toxic treatments. Moreover, an assay for the presence of lymph node metastases could be used to detect recurrence of PTC, to follow the course of PTC, or to monitor the effectiveness of a treatment regimen for PTC. Such an assay would help improve individualized treatment for this cancer.

Several groups have performed expression profile analysis of metastatic primary PTC or in vitro model systems to identify clinical outcome markers (5, 6). Although these approaches might identify useful prognostic markers, they do not directly identify gene expression changes that occur in the metastatic cells. Identification of genes that are consistently expressed in metastatic PTC cells could yield useful biomarkers, which could be useful not only for prognosis, but also to identify occult metastatic cells in lymph node biopsies, etc. In addition to the practical uses as markers, genes associated with metastasis could help reveal the molecular mechanisms of the metastatic process.

DESCRIPTION OF THE INVENTION

Figure 1:
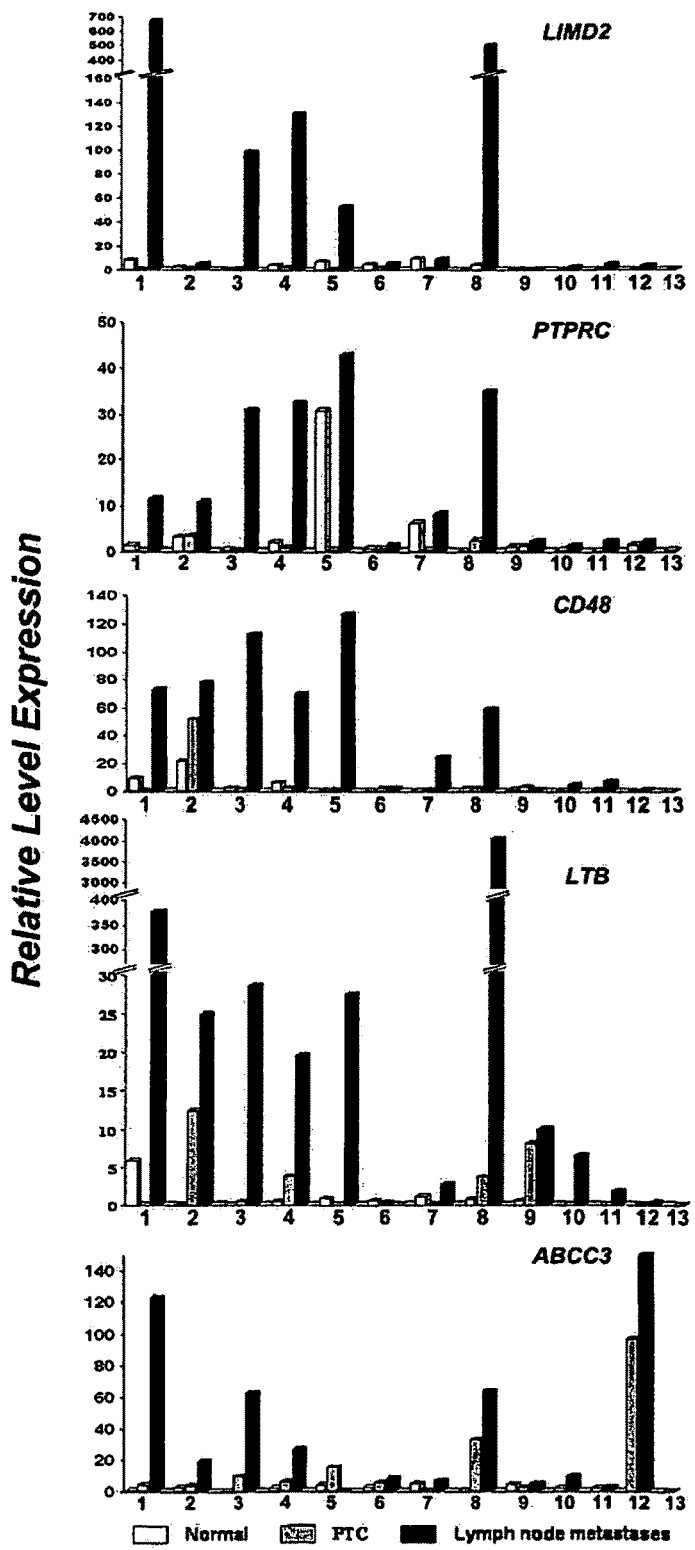
FIG. 1 shows relative levels of expression determined by qPCR in matched-samples of normal thyroid (white bar), papillary thyroid carcinoma (gray bars) and lymph node metastases (black bars) (samples 1-9), matched normal and metastases (samples 10 and 11) and matched tumor and metastases (sample 12) and normal lymph node (sample 13). Transcript levels were normalized to the average of RS8 and QP-C control genes, which were uniformly expressed in all 3 thyroid SAGE libraries. Numbers correspond to cases described in Table 1. The qPCR data were log (2) transformed for statistical analysis. The paired t-test (normal vs. metastases) showed that PTPRC ($P=0.001$), LIMD2 ($P=0.0016$), LTB ($P=0.00096$) and CD48 ($P=0.00042$). ABCC3 ($P=0.0094$) was very close to the significance. The paired t-test (tumor vs. metastases) showed that PTPRC ($P=0.00059$) and LIMD2 ($P=0.00056$) expression was significantly different at the 0.05 level.

The present inventors have identified proteins, and the mRNAs encoding them, which are present at high levels in lymph node metastases of papillary thyroid carcinoma (PTC), but which are not present, or are present at a very low level, in the lymph nodes of normal (non-cancerous) subjects. These expression products (the proteins or the mRNAs encoding them) can serve as markers for the presence of lymph node metastases in subjects having a PTC.

This invention relates, e.g., to a method for detecting the presence of lymph node metastases (metastatic cells) in a subject having PTC. The method comprises measuring in a sample from the subject the amount of expression [e.g., as represented by the amount of a protein (one form of expression product), or the amount of mRNA encoding the protein (another form of expression product)] of one or more of the following proteins: (a) LIMD2, and/or (b) PTPRC (sometimes referred to as CD45 or LCA), and/or (c) LTB, and/or (d) CD48, and/or (e) ABCC3, compared to a baseline value, wherein a significant amount (e.g., a statistically significant amount) of over-expression of one or more of proteins (a)-(e), compared to the baseline value, indicates that lymph node metastases are likely to be present in the subject (the PTC is likely to have undergone metastasis to a lymph node). The amount of expression may be determined for any combination of 1, 2, 3, 4, or all 5 of these proteins. These five proteins are sometimes referred to herein as "proteins of the invention."

A summary of the full names and the functions or properties of proteins discussed herein is provided in Table 2. The nucleotide and amino acid sequences of the proteins of the invention, and the nucleic acids encoding them, are well-known and can be determined routinely, as well as downloaded from various known databases. See, e.g., the world wide web site, ncbi.nlm.nih.gov. or the GenBank Accession numbers provided in Table 2.

In one embodiment of the invention, the sample is from a lymph node biopsy from the subject. An assay of the invention can be used to detect metastases, including occult (hidden) metastases, in such lymph nodes. Alternatively, the sample can be a serum sample.

The amount of expression of a protein of the invention can be determined by measuring the amount of the protein, or by measuring the amount of mRNA encoding the protein. The amount of a protein can be determined using an antibody. For example, the method can encompass binding the protein to an antibody which is specific for it, under conditions that are effective for specifically binding the protein to the antibody. In one embodiment of the invention, the antibody is contacted with a histological preparation (e.g. from a lymph node biopsy), and the amount of protein is determined by immunohistochemical staining. The amount of an mRNA can be determined using a nucleic acid probe for the mRNA. For example, the method can encompass hybridizing the mRNA to a nucleic acid probe which is specific for it, under conditions that are effective for specifically hybridizing the mRNA and the probe.

In one embodiment of the invention, if a subject is determined by a method of the invention to be likely to have lymph node metastases, the subject is then treated aggressively for the PTC, using conventional aggressive treatment methods; but if the subject is determined by a method of the invention not to be likely to have lymph node metastases, the subject is not treated aggressively for the PTC.

A detection (diagnostic) method of the invention can be adapted for many uses. For example, it can be used to follow the progression of a PTC, or to monitor a subject for a recurrence of the cancer. In one embodiment of the invention, the detection is carried out both before (or at approximately the same time as), and after, the administration of a treatment, and the method is used to monitor the effectiveness of the treatment. A subject can be monitored in this way to determine the effectiveness for that subject of a particular drug regimen; or a drug or other treatment modality can be evaluated in a pre-clinical or clinical trial. In these methods, an increase in the expression of a marker of the invention compared to a baseline value is indicative of progression or recurrence of the disease; and a decrease in the expression of a marker of the invention compared to a baseline value is indicative of effective treatment.

Another embodiment of the invention is a kit for detecting the presence of lymph node metastases in a subject having PTC, comprising reagents for detecting the amount of expression of (a) LIMD2, and/or (b) PTPRC, and/or (c) LTB, and/or (d) CD48, and/or (e) ABCC3. Any suitable combination of these reagents can be present in a kit of the invention.

The expression of any combination of the proteins examined herein, or others, can be assayed with a method of the invention. For example, one can first measure the amount of expression of LIMD2 compared to a baseline value, to determine if a subject exhibits a likelihood of having lymph node metastases. One can then further measure the amount of expression of PTPRC and/or LTB compared to the baseline value. A significant increase in the amount of expression of PTPRC and/or LTB compared to the baseline value indicates a greater likelihood that lymph node metastases are present in the subject. In addition, one can further measure the amount of expression of CD48 and/or ABCC3. A significant increase in the amount of expression of CD48 and/or ABCC3 compared to the baseline value indicates an even greater likelihood that lymph node metastases are present in the subject. Any combination of proteins, including 1, 2, 3, 4, or 5 of the above-mentioned proteins, or others, can be measured by a method of the invention.

The markers validated herein were positive not only in lymph node metastases from classical PTC but also in metastases from the follicular variant of PTC (independent of BRAF mutation status). It is expected that markers of the invention can be used to detect lymph node metastases from a variety of cell thyroid subtypes, including medullary and follicular.

In addition to the proteins studied herein, the level of expression of serum thyroglobulin (TG) can also be used in a method of the invention, e.g. for monitoring PTC disease progression in the clinic. Monitoring of serum TG levels has been used as a gold-standard method in the follow-up of patients after total thyroidectomy and radioiodine therapy. However, the value of this immunoassay is limited to patients with total thyroidectomy. Interference by antithyroglobulin antibodies in the blood is also present in approximately 25% of patients. Circulating thyroid-specific transcripts such as TG, TPO, TSHR, NIS and PDS have been suggested as potential molecular markers of residual or recurrent thyroid cancer (40-42). Conversely, several reports suggested that these markers could not be used in the follow-up of patients (43, 44). Therefore there is a need for better markers. The new markers described herein can be used in conjunction with thyroglobulin (or alone), e.g. in the follow-up of patients with thyroid tumor recurrence.

By a "sample" (e.g. a test sample) from a subject having PTC is meant a sample that is suspected of comprising metastatic cells. The sample may be, e.g., from a biopsy of a lymph node or a primary thyroid tumor, or from serum, or from other tissues that will be evident to a skilled worker. In addition to the findings reported herein that markers of the invention are significantly overexpressed in lymph node metastases, the inventors have also found that markers of the invention are expressed in intra-thyroidal metastases (e.g., metastatic spread within a tumor, such as micrometastases to the contralteral lobe). Therefore, samples from primary thyroid tumors (e.g., the portion removed during surgery) are expected to provide useful tissue for diagnosis of metastases. Such samples can be assayed by immunohistochemical assays on the tissue, using an antibody against one or more of the proteins of the invention. Furthermore, it is expected that, like most cancers, tumor cells, including cells from metastatic tumors, are shed into the blood stream. Therefore, assays of serum samples (molecular detection of circulating tumor cells or markers of the invention) is expected to represent a new approach for improving early diagnosis of metastasized PCT. Protein markers or the nucleic acids encoding them in such samples can be assayed using any of the immunoassays or the assays for nucleic acid expression described herein except, of course, for immunohistochemical assays.

Methods for obtaining samples and preparing them for analysis (e.g., for detection of the amount of protein or mRNA encoding the protein) are conventional and well-known in the art.

A "subject," as used herein, includes any animal that has a PTC. Suitable subjects (patients) include laboratory animals (such as mouse, rat, rabbit, or guinea pig), farm animals, and domestic animals or pets (such as a cat or dog). Non-human primates and, preferably, human patients, are included.

As used herein, a "baseline value" refers to the expression, as determined by the levels (amounts) of mRNA and/or protein, in normal tissue (e.g., the same type of tissue as the tested tissue, such as normal lymph node or normal serum), from normal subjects that do not have PTC. If desired, a pool of the same tissues from normal subjects can be used. Such baseline values may be available in a database compiled from the values and/or may be determined based on published data or on retrospective studies of patients' tissues, and other information as would be apparent to a person of ordinary skill implementing a method of the invention. Suitable baseline values may be selected using statistical tools that provide an appropriate confidence interval so that measured levels that fall outside the standard value can be accepted as being aberrant from a diagnostic perspective, and predictive of the presence of lymph node metastases.

A significantly elevated amount of an mRNA or a protein of the invention compared to this baseline value, then, indicates that a test subject is likely to harbor lymph node metastases (that lymph node metastases are likely to be present in the test subject). Of course, for the few proteins described herein, such as PTPR4, whose expression is decreased in subjects that have lymph node metastases, a significantly reduced amount of the protein or mRNA encoding it indicates that a test subject is likely to harbor lymph node metastases.

A "significant" increase in the amount of a protein or mRNA, as used herein, can refer to a difference which is reproducible or statistically significant, as determined using statistical methods that are appropriate and well-known in the art, generally with a probability value of less than five percent chance of the change being due to random variation. Some such statistical tests are described in the Examples herein. For example, a significant increase in the amount of mRNA or protein compared to a baseline value can be at least about 2.5-fold (e.g., at least about 5-fold, 10-fold, 20-fold, 25-fold, or more) higher.

For some assays, such as immunohistochemical assays, it may be more difficult to quantify the degree of increase in a positive test. For immunohistochemical assays, quantitation can be performed by counting the number of positive staining cells per microscopic field. IHC is normally reported semi-quantitatively. Typically, a clinical report indicates the number of lymph nodes which have metastatic cells. For example, a report can indicate that two of eight nodes examined tested positive for the LIMD2 protein. Alternatively, the number of positive cells within sections can be counted. In general, the detection of any metastatic cells in the lymph nodes tested is considered to be a positive (significant) result and warrants making a decision to treat a subject aggressively.

A significant increase in the amount of expression of a marker of the invention compared to the baseline value indicates that lymph node metastases are likely to be present in the subject. A subject that is "likely" to have lymph node metastases has greater than, e.g., at least about: a 25%, more likely 50%, 75%, most likely 90% chance to have the metastases.

The amount of a protein can be measured using any suitable method. Some methods involve the use of antibodies specific for a protein of interest. Antibodies suitable for use in such assays are commercially available, or can be prepared routinely. Methods for preparing and using antibodies in assays for proteins of interest are conventional, and are described, e.g., in Green et al., Production of Polyclonal Antisera, in *Immunochemical Protocols* (Manson, ed.), (Humana Press 1992); Coligan et al., in *Current Protocols in Immunology*, Sec. 2.4.1 (1992); Kohler & Milstein (1975), *Nature* 256, 495; Coligan et al., sections 2.5.1-2.6.7; and Harlow et al., Antibodies: A Laboratory Manual, page 726 (Cold Spring Harbor Laboratory Pub. 1988). The antibody against LIMD2 used in the Examples herein was a gift from the laboratory of Dr. Frank Rauscher.

Any of a variety of antibodies can be used in methods of the invention. Such antibodies include, e.g., polyclonal, monoclonal (mAbs), recombinant, humanized or partially humanized, single chain, Fab, and fragments thereof. The antibodies can be of any isotype, e.g., IgM, various IgG isotypes such as $IgG_1$, $IgG_{2a}$, etc., and they can be from any animal species that produces antibodies, including goat, rabbit, mouse, chicken or the like. The term, an antibody "specific for" a protein, means that the antibody recognizes a defined sequence of amino acids, or epitope, in the protein, and binds selectively to the protein and not generally to proteins unintended for binding to the antibody. The parameters required to achieve specific binding can be determined routinely, using conventional methods in the art.

In one embodiment of the invention, antibodies specific for a (one or more) protein of the invention are immobilized on a surface (e.g., are reactive elements on an array, such as a microarray, or are on another surface, such as used for surface plasmon resonance (SPR)-based technology, such as Biacore), and proteins in the sample are detected by virtue of their ability to bind specifically to the antibodies. Alternatively, proteins in the sample can be immobilized on a surface, and detected by virtue of their ability to bind specifically to the antibodies. Methods of preparing the surfaces and performing the analyses, including conditions effective for specific binding, are conventional and well-known in the art.

Among the many types of suitable immunoassays are immunohistochemical staining, ELISA, Western blot (immunoblot), immunoprecipitation, radioimmunoassay (RIA), fluorescence-activated cell sorting (FACS), etc. Assays used in a method of the invention can be based on colorimetric readouts, fluorescent readouts, mass spectroscopy, visual inspection, etc. Assays can be carried out, e.g., with suspension beads, or with arrays, in which antibodies or cell or blood samples are attached to a surface such as a glass slide or a chip.

In one embodiment of the invention, a histological sample is obtained from a subject (e.g., from a lymph node biopsy), using any method known in the art, and is stained with a suitable antibody in a conventional immunohistochemical assay. Some typical assays are described in the Examples herein.

The amount of an mRNA encoding a protein of the invention can be measured using any suitable method. Examples of such methods include, e.g., reverse transcriptase-polymerase chain reaction (RT-PCR), including real time PCR, microarray analysis, Northern blot analysis, differential hybridization, and ribonuclease protection assay. Such methods are well-known in the art and are described, e.g., in Sambrook et al., Molecular Cloning: A Laboratory Manual, current edition, Cold Spring Harbor Laboratory, Cold Spring Harbor, N.Y., and Ausubel et al., Current Protocols in Molecular Biology, John Wiley & sons, New York, N.Y.

In one embodiment of the invention, an mRNA of interest is detected by hybridizing the mRNA or a cDNA generated from the mRNA (the two are referred to here as a nucleic acid) to a nucleic acid probe that is specific for the nucleic acid, under conditions that are effective for specific hybridization of the nucleic acid to the probe. The probe may be a full-length complement of the nucleic acid, or a fragment that can be as small as about 10 base pairs, or any size in between, provided that the probe hybridizes specifically to the nucleic acid of interest (such that probes that are specific for particular nucleic acids from the sample are specifically hybridized to those nucleic acids). Methods for designing nucleic acid probes that are specific for a nucleic acid of interest are conventional and well-known in the art.

A probe that is "specific for" a nucleic acid (e.g., an mRNA or cDNA) contains sequences that are substantially similar to (e.g., hybridize under conditions of high stringency to) one of the strands of the nucleic acid. By hybridizing "specifically" is meant herein that the two components (the mRNA or cDNA and the nucleic acid probe) bind selectively to each other and not generally to other components unintended for binding to the subject components. The parameters required to achieve specific binding can be determined routinely, using conventional methods in the art.

As used herein, "conditions of high stringency" or "high stringent hybridization conditions" means any conditions in which hybridization will occur when there is at least about 95%, preferably about 97 to 100%, nucleotide complementarity (identity) between a nucleic acid of interest and a probe. Generally, high stringency conditions are selected to be about 5° C. to 20° C. lower than the thermal melting point ($T_m$) for the specific sequence at a defined ionic strength and pH. Appropriate high stringent hybridization conditions include, e.g., hybridization in a buffer such as, for example, 6×SSPE-T (0.9 M NaCl, 60 mM $NaH_2 PO_4$, 6 mM EDTA and 0.05% Triton X-100) for between about 10 minutes and about at least 3 hours (in one embodiment, at least about 15 minutes) at a temperature ranging from about 4° C. to about 37° C.). In one embodiment, hybridization under high stringent conditions is carried out in 5×SSC, 50% deionized Formamide, 0.1% SDS at 42° C. overnight.

In one embodiment of the invention, the probes are arrayed on a suitable surface, such as a chip, e.g. in an array.

A method of the invention can be used to stage PTCs. For example, if a subject is determined by a method of the invention to be likely to have lymph node metastases, a decision can be made to treat the subject with an aggressive form of treatment; and, in one embodiment, the treatment is then administered. Suitable aggressive treatment modalities include, for example, radiation, chemotherapy, additional surgery, immunotherapy or other forms of targeted therapy. By contrast, if a subject is determined not to be likely to have lymph node metastases, a decision can be made to adopt a less aggressive treatment regimen; and, in one embodiment, the subject is then treated with this less aggressive forms of treatment. Suitable less aggressive forms of treatment include, for example, just observing the patient, or performing less extensive surgery (e.g., a lobectomy, rather than near-total thyroidectomy, or no dissection of lymph nodes) than is performed in aggressive therapies. A subject that does not have lymph node metastases is thus spared the unpleasant side-effects associated with the unnecessary, more aggressive forms of treatment. By "treated" is meant that an effective amount of a chemotherapeutic drug or other anti-cancer procedure is administered to the subject. An "effective" treatment refers to a treatment that elicits a detectable response (e.g. a therapeutic response) in the subject.

One aspect of the invention is a kit for detecting whether a subject having PTC is likely to have lymph node metastases, comprising one or more agents for detecting the amount of expression of a protein of the invention [e.g., the amount of the protein, and/or the amount of a nucleic acid (e.g., an mRNA) encoding the protein]. As used herein, the singular forms "a," "an" and "the" include plural referents unless the context clearly dictates otherwise. For example, "a" protein of the invention, as used above, includes 1, 2, 3, 4, 5 or more of the proteins. The agents in the kit can encompass, e.g., antibodies specific for the proteins, or probes specific for the mRNA that can be used to hybridize to the RNA (or to a cDNA generated from it) or to perform RT-PCR. The kit may also include additional agents suitable for detecting, measuring and/or quantitating the amount of protein or nucleic acid. Among other uses, kits of the invention can be used in experimental applications. A skilled worker will recognize components of kits suitable for carrying out a method of the invention.

Optionally, a kit of the invention may comprise instructions for performing the method. Optional elements of a kit of the invention include suitable buffers, containers, or packaging materials. The reagents of the kit may be in containers in which the reagents are stable, e.g., in lyophilized form or stabilized liquids. The reagents may also be in single use form, e.g., for the performance of an assay for a single subject.

In the foregoing and in the following examples, all temperatures are set forth in uncorrected degrees Celsius; and, unless otherwise indicated, all parts and percentages are by weight.

EXAMPLES

Example I

Materials and Methods

A. Generation of SAGE libraries. Matched tissues of a normal thyroid (NT), a papillary thyroid carcinoma (PTC) and its lymph node metastasis (LNM) were chosen for SAGE (Case 1, Table 1). This matched set was chosen in part because the sample quality was high, measured by the high percentage of tumor cells observed by H & E histopathology performed on frozen sections from primary and metastatic tumors. The primary sample was from the tumor core, in an attempt to avoid the capsule and surrounding normal tissue. To eliminate the expression of normal lymph node cells without any metastasis a SAGE library was generated from a normal lymph node (NL) (Stratagene La Jolla, Calif., USA). The libraries were constructed using NlaIII as the anchoring enzyme as described in the original SAGE procedure (7) and the ditag containing plasmid inserts were sequenced through the SAGE portion of the Cancer Genome Anatomy Project (8). Tags were extracted from sequence text files and processed to remove duplicate ditags, linker sequences and repetitive tags using SAGE 2002 software version 4.12 (available at the world wide web site www.sagenet.org). The full set of tag counts for all 4 libraries is available for downloading or analysis at the SAGE Genie Web site at the world wide web site cgap.nci.nih.gov/SAGE (9).

TABLE 1

Summary of clinical data

| Cases | Diagnosis | Sex | Age at Diagnosis (years) | Nodule size (cm) | Extrathyroidal extension | Metastasis at presentation | Metastasis (Follow up) | Persistent disease | Iodine | BRAF Mutation Lymph node Metastases |
|---|---|---|---|---|---|---|---|---|---|---|
| 1. | *PTC[A] | F | 19 | 3.5 | N | Y | Y | Y | Y | V600E + K601del |
| 2. | FVPTC[A] | F | 76 | 1.0 | N | Y | Y | Y | Y | V600E |
| 3. | PTC[A] | M | 41 | 1.5 | Y | Y | NA | Y | Y | V600E |
| 4. | PTC[A] | F | 55 | 2.5 | Y | Y | N | N | Y | V600E |
| 5. | FVPTC[A] | F | 52 | 5.0 | Y | Y | N | N | Y | N |
| 6. | PTC[A] | F | 29 | 3.5 | Y | Y | NA | Y | Y | V600E |

TABLE 1-continued

Summary of clinical data

| Cases | Diagnosis | Sex | Age at Diagnosis (years) | Nodule size (cm) | Extrathyroidal extension | Metastasis at presentation | Metastasis (Follow up) | Persistent disease | Iodine | BRAF Mutation Lymph node Metastases |
|---|---|---|---|---|---|---|---|---|---|---|
| 7. | PTC[A] | F | 39 | NA | Y | Y | NA | NA | NA | V600E + K601del |
| 8. | FVPTC[A] | F | 49 | 2.0 | Y | Y | Y (lung) | Y | Y | N |
| 9. | PTC[A] | F | 49 | 2.2 | Y | Y | NA | Y | Y | ND |
| 10. | PTC[B] | F | 46 | 1.7 | Y | Y | N | N | Y | V600E |
| 11. | PTC[B] | F | 42 | 1.5 | Y | Y | NA | Y | Y | V600E |
| 12. | FVPTC[C] | F | 15 | 4.5 | Y | Y | NA | NA | NA | N |
| Second.validation set | | | | | | | | | | |
| 13 | PTC[A] | M | 34 | 5.5 | Y | Y | Y | N | Y | V600E + K601del |
| 14. | PTC[A] | M | 62 | 2.8 | Y | Y | Y | Y | Y | ND |
| 15. | PTCA[A,D] | M | 34 | 0.7 | Y | Y | Y | Y | Y | ND |
| 16. | FVPTCA[A,D] | M | 23 | 1.3 | Y | Y | Y | Y | Y | ND |
| 17. | PTC[A,D] | F | 19 | 3.5 | N | Y | Y | Y | Y | ND |
| 18. | PTC[C] | F | 33 | 1.2 | N | Y | N | N | Y | ND |

*Case 1 was chosen for SAGE
Papillary thyroid carcinoma (PTC); follicular variant of papillary thyroid carcinoma (FVPTC).
[A]Matched-normal, tumor and lymph node metastasis.
[B]Matched-normal and lymph node metastasis.
[C]Matched-tumor and lymph node metastasis.
[D]Lymph node metastases obtained during re-operation for recurrence
Not available (NA). Yes (Y). No (N)

B. SAGE analysis. The metastasis-derived library was compared with primary tumor using SAGE 2000 software. Pairwise and Monte-Carlo simulations were used to identify transcripts which difference was statistically different at P value of $\leq 0.001$. Transcripts that were over-expressed in the metastasis library when compared to primary tumor and, therefore, candidate genes as associated with metastasis process, were assessed in LNM and LN libraries.

C. Tissue samples for validation of candidate genes. To test our hypothesis, the metastasis candidate genes were first analyzed in a series of matched normal thyroid tissue, primary PTC and lymph node metastasis provided by the Hospital das Clinicas, Universidade de Sao Paulo. The neck dissection was performed by a single surgeon during thyroidectomy procedure. All samples were collected and frozen immediately after surgical biopsy and stored at −80° C.

Tissue histology of Haematoxylin and Eosin stained, from paraffin-embedded sections obtained from frozen samples, was evaluated by an experienced pathologist and used to confirm the initial diagnosis (Table 1). This histology was also used to determine percentage of tumor cells and only cases containing high percentage of tumor cells in both primary tumor and metastasis were considered for validation. Using this criterion, 12 series were selected: 9 matched-normal thyroid, PTC and LNM; 1 paired PTC and LNM and 2 paired NT and LNM (Table 1, First Validation Set). Additionally, a normal lymph node was included as a negative control.

For further confirmation of metastasis genes, a second validation set of paraffin-embedded sections was obtained from 6 matched samples of normal lymph nodes, normal thyroid, primary tumor and lymph node metastasis (Table 1, Second Validation Set). The follow-up of these patients showed that 3 out of 6 patients had regional recurrence (cases 15-17, Table 1). There were at least two lymph nodes with metastasis studied from each case in the second validation set. Additionally, in the three patients who recurred at least two more lymph nodes were studied from the recurrence. A total of 20 lymph node metastases were investigated. A third set of samples included 15 primary classical and follicular variant of PTC (metastatic and non-metastatic tumors, not shown in Table 2). The paraffin-embedded sections were selected from the archives of the Department of Pathology, Federal University of Sao Paulo. The study was approved by the Ethic and Research Committees from both Universities and was conducted in accordance with the Declaration of Helsinki Principles.

D. RNA isolation, cDNA synthesis and GPCR. Total RNA was isolated Trizol (Invitrogen Corp., Carlsbad, Calif.). One microgram of total RNA was treated with a DNAse (Ambion, Austin, Tex.) and was reverse-transcribed to cDNA using Super-Script II Reverse Transcriptase kit with an oligo $(dT)_{12-18}$ primer and 10 units of RNase inhibitor (Invitrogen Corp). An aliquot of cDNA was used in 20 μl PCR reactions containing TaqMan universal PCR master mix, 10 μM of each specific primer and FAM-labeled probes for the target genes or reference gene (QP-C) and VIC-labeled probe for the second reference gene (RS8) (TaqMangGene Assays on Demand; Applied Biosystems, Foster City, Calif.). Quantitative PCR reactions were performed in triplicate, the threshold cycle (Ct) was obtained using Applied Biosystem software (Applied Biosystems) and were averaged (SD 1). Relative expression levels were calculated according to the formula $2^{(Ce-Re)}/2^{(Cn-Rn)}$, where Ce is the Ct cycle number observed in the experimental sample for controls genes, Re is the Ct cycle number observed in the experimental sample for the reference gene, Cn is the average Ct cycle number observed in the normal thyroid tissues for control genes, and Rn is the average Ct cycle number observed in the normal thyroid tissues for the reference gene (10, 11). The results obtained from relative expression levels were log transformed and used for statistical analysis. Representative results are shown in FIG. 1.

E. Statistical Analysis. The first objective of this analysis was to determine if the expression values, as measured by qPCR, for 11 genes were different between tumor and metastases (n=10 pairs) or between normal and metastases (n=11 pairs), using paired data (Table 1). The comparison of the expression levels was carried out using a paired Student's t test. In order to correct for multiple tests, a Bonferroni correction was used. A comparison was designated as statistically significant if the t statistic was found to be significant, using an alpha level that had been adjusted (using a Bonferroni adjustment) to keep the family-wise error rate at 0.05. A one-sided test was used because of the expectation that the gene expression in the metastatic samples would be higher than the gene expression in the tumor or normal samples. The second objective was to determine whether a class predictor (tumor versus metastasis) could be developed using the qPCR data from these 11 genes. To investigate the development of an expression based predictor that could be used to predict tumor or metastatic class, we followed the framework outlined by Radmacher et al. (2002), using the compound covariate predictor for gene expression data (12, 13). The performance of the predictor was tested using leave one out cross validation for all steps of the prediction procedure (i.e., selection of differentially express genes as well as creation of the prediction rule) (12, 14). We assessed the significance of the performance of the predictor using the permutation based test outlined by Radmacher et al. (2002), in which the class labels were randomly permuted and the proportion of data sets that had a cross validated error rate and small as the error rate observed in the data set was calculated (12). The only difference in the permutation test from that used by Radmacher et al. (2002) was that, since the data were paired in the present study, we used a paired permutation. In addition, because of the small size of the data set, we were able to generate the complete permutation distribution.

F. Immunohistochemical analysis. Three-µM sections were deparaffinized and rehydrated through a graded series of ethanols. Endogenous peroxidase was quenched using a 3% solution of hydrogen peroxide in methanol for 30 min. Steaming retrieval was performed in buffer AR-10 (BioGenex, San Ramon, Calif., USA) for 10 min and then allowed to cool for 30 min. The sections were incubated with primary antibodies for at least 16 h at 4° C. followed by incubation with the labeled polymer DAKO EnVision™+ System, HRP (Dako laboratories, Carpinteria, Calif.). Hematoxylin was used as the nuclear counterstain. Anti-CD45 (T29/33; DaKo laboratories) was used at a dilution of 1:800 and anti-LTP (FL244; Santa Cruz Biotechnologies) at a dilution of 1:50. The control for antibody specificity included incubation with rat IgG used at the same concentration as the first antibody. Positive and negative controls were used in each run. All slides were scored in a blinded fashion with immunopositivity evaluated semiquantitatively as follows: negative (−) when less than 10% of the cells were immunoreactive and positive (+) when more than 10% of cells were immunoreactive. Immunohistochemical staining was evaluated independently by two investigators.

Example II

Analysis of SAGE Data

A total of 481,775 SAGE tags were obtained from 4 libraries, representing 160,951 unique transcript tags. The number of SAGE tags per library ranged from 99,911 (NL) to 143,689 (PTC). Tag numbers were normalized to 200,000-tags/library.

To identify genes potentially involved in metastasis, a comparison between primary tumor and LNM libraries was performed. Monte Carlo simulations yielded 498 tags statistically significant at P value of $\leq 0.001$ or 319 tags at a P value of 0.0001. Thirty-one of the 498 transcripts were highly expressed in the metastasis library and not expressed or expressed at low levels in primary tumor, while 47 transcripts were under-expressed in the metastasis library. To refine our analysis, the transcript expression of the metastasis-associated genes was assessed in the normal lymph node and normal thyroid libraries. Those transcripts with the greatest fold-induction in metastasis library were chosen for validation by qPCR because they could not only help better understand the metastatic process, but also had potential as prognostic markers. Additionally, we chose three genes (MET, LSM7 and S100A11) whose expression was previously reported in primary tumors with metastatic potential, although expression within the metastasis was not reported (15-17). Table 2 lists the eleven transcripts selected for validation and their tag counts in our four SAGE libraries. For comparison we show in Table 2 the transcript levels for those genes known to be involved in normal thyroid physiology. According to gene ontology databases, the differentially expressed genes are mainly involved in transport and cell signaling.

Among the transcripts highly expressed in lymph node metastasis library and not expressed in primary tumor were 6 transcripts (CXCR4, SNC73, PRSS1, CXCL13, STAT5A and SDC1) that were previously associated with invasion and metastases in other cancers. Although not selected for validation by qPCR or IHC, SAGE analysis suggested that their expression correlated with metastasis in this patient (P<0.001). Further analysis is expected to confirm that these genes play a role in lymph node metastasis of PTC.

Example III

Relative Levels of Gene Expression for Selected Candidate Genes

We used qPCR to test the expression of the transcripts shown in Table 1 in matched sets of normal thyroid, primary PTC and lymph node metastases. This was the first validation set. We compared the results obtained from SAGE with the qPCR results for the samples used to generate NT, PTC and LNM libraries (Case 1, Table 1 and FIG. 1). When the initial samples were used, the difference predicted by SAGE was confirmed for all 11 genes.

PTPRC was found over-expressed in all metastases analyzed when compared with paired normal thyroid and primary tumor (samples 1-12, FIG. 1) and normal lymph node (sample 13, FIG. 1). LIMD2 and CD48 were consistently expressed in the lymph node-metastases and were not expressed in the normal lymph node (sample 13, FIG. 1) and not expressed or expressed at very low levels in most of matched normal thyroid tissues and/or primary tumors.

LTB and ABCC3 were remarkably higher in all metastases and expressed at much lower levels in a number of primary tumors tissues (FIG. 1). Although CS77 expression was elevated in the majority of paired primary tumor, its expression was markedly higher in the lymph node metastases. Therefore, some genes analyzed here may start expression earlier than at the onset of metastasis, but still prove useful as markers of metastasis.

LSM7 and SYT12 showed similar level of expression in normal thyroid, primary tumor and LNM in most samples tested. Contrary results were obtained for PTPN4. The validation data showed that PTPN4 was under-expressed in most lymph node metastases rather than over-expressed.

For those genes previously reported to be associated with metastasis, but not implicated in the late stages of metastasis by our SAGE data, qPCR data also showed lack of overexpression in the metastases. For example, S100A11 was observed in lymph node metastases and its expression was higher in most primary tumors than in the matched metastases. MET was expressed in high levels in about 60% of lymph-node metastases analyzed and in intermediate levels in primary tumors from these cases. In the remaining cases, however, the expression level of MET was higher in primary tumor and normal thyroid tissue than in corresponding metastases. Although we did not find MET specific for metastasis, our results are in agreement with the literature where MET was found over-expressed in about 60-70% of metastatic primary PTC (18, 19).

Example IV

Statistical Analysis

In the first comparison PTPRC, LIMD2, LTB and CD48 were found to be significantly different between the normal and metastatic samples (p value<0.0045). PTPRC and LIMD2 were found to be statistically significant between tumor and metastatic classes (p value<0.0045).

The second analysis determined whether a subset of these 11 genes could be used to predict metastasis versus tumor class. The class predictor used genes whose expression levels were declared significantly different at the 0.05 family-wise error level using the t-test (p value<0.0045). The sample t statistics were used as weights in the compound covariate predictor (Radmacher et al. 2002). To evaluate the predictor we used leave one out cross validation: for each run, one tumor-metastatic pair of samples was left out, and the predictor developed on the remaining nine pairs of samples. The two left out samples were predicted. We used all the steps of the prediction procedure, including selection of differentially expressed genes, as well as creation of the prediction rule (Simon et al. 2003). Using leave one out cross validation, four of the 20 samples were misclassified for a prediction accuracy of 80% with a 95% two sided confidence interval of [0.56, 0.94]. To assess the significance of these prediction results, we implemented a permutation test. The proportion of random permutations which classified four or fewer miss classifications was 0.013. Thus, the results of the prediction analysis are statistically significant. PTPRC and LIMD2 were always selected in each step of the cross validation procedure (10 out of 10 times i.e., each time a pair of samples was left out).

Example V

Immunohistochemical Analysis

To ascertain if our candidate metastasis-associated markers had increased protein levels in the lymph node metastatic cells compared to other tissues, IHC analysis was performed in a second validation set of paired-normal lymph node, normal thyroid, primary tumor and lymph node metastases (Table 1). IHC analysis was performed for PTPRC (CD45) and LTB.

Figure 2:
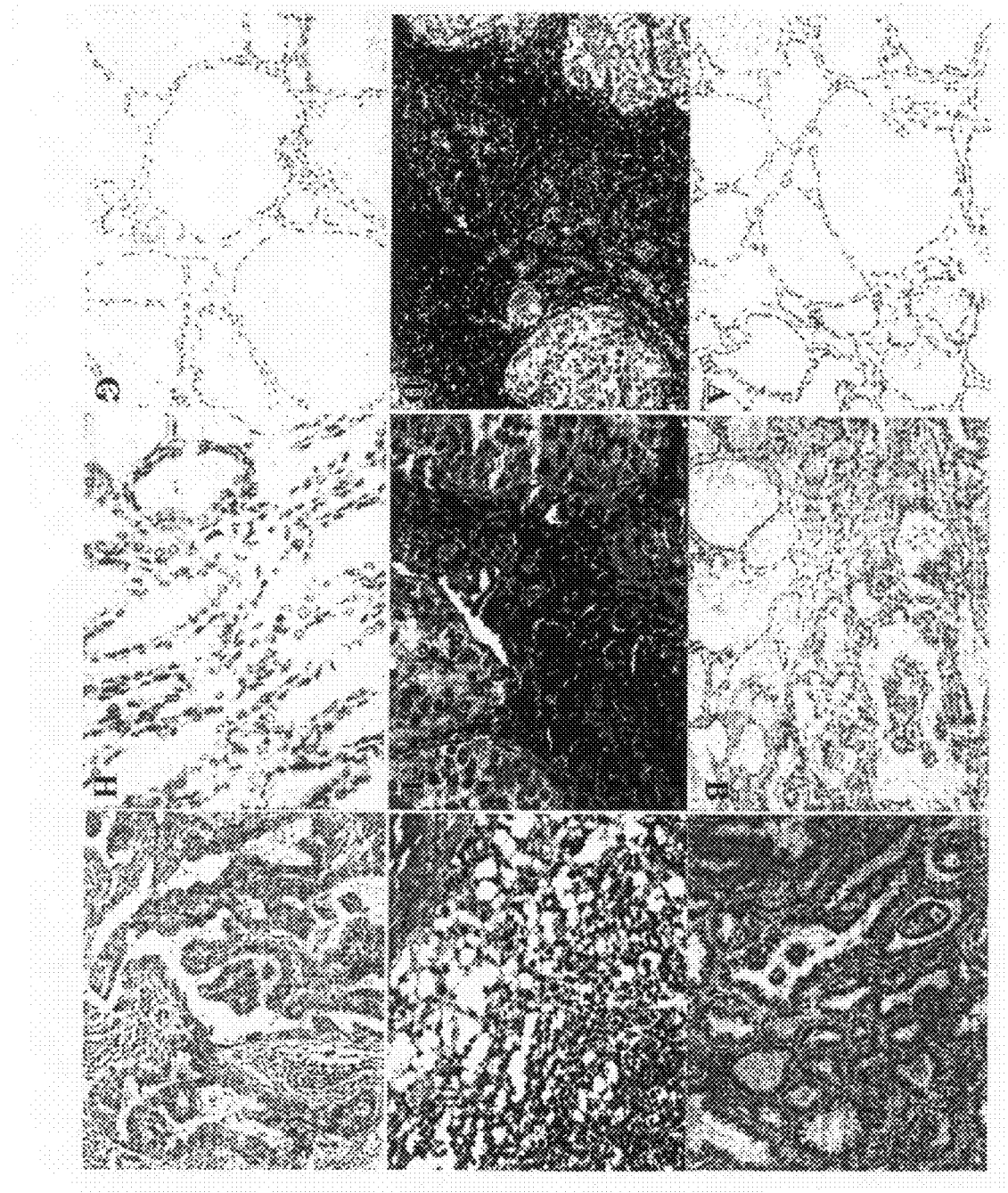
FIG. 2 shows representative results of immunohistochemical analysis. There was no PTPRC reactivity observed in normal thyroid (A) and primary tumors (B and C). Strong brown staining for PTPRC was observed in the surrounding immune cells in metastatic lymph node (D and E). Lymphocytes were positive for PTPRC in normal lymph node (F), but with a different pattern and intensity from that in E and F. No staining for LTB was observed in normal lymph node, normal thyroid lesion (G), most of primary tumors (H) and the surrounding immune cells (I). LTB was positive for tumor cells within a lymph node, as revealed by the brown immunostaining (I). Original magnification is ×200 (A-D and I) and ×400 (E-G and H).

As demonstrated by qPCR, PTPRC, also named CD45 or LCA, was highly expressed in lymph node metastases and was not expressed in matched normal thyroid and primary tumors. In the metastatic lymph nodes, a strong staining was observed in lymphocytes rather than in the metastatic cancer cells. Of note, lymphocytes were the predominant cells in the metastatic lymph node, compared to normal lymph node, which may explain the strong brown staining observed (FIG. 2) and the qPCR results (FIG. 1). To ascertain that PTPRC was found expressed at lower levels in the normal lymph nodes, we additionally investigated the expression of PTPRC in 6 normal auxillary's lymph nodes. Although PTPRC expression was found in the lymphocytes in the normal lymph nodes, the number of lymphocytes with positive expression of PTPRC was inferior to the metastatic lymph node (FIG. 2).

We further assessed the expression of PTPRC in 15 primary PTCs (follicular variant and classical). IHC analysis revealed that 13 out of 15 PTCs were negative for PTPRC. In one case, however, tumor-infiltrating lymphocytes were positive. In the remaining case of papillary thyroid carcinoma with a trabecular-insular area, a focal staining was observed in the epithelial cells.

qPCR data showed that LTB was highly expressed in most lymph nodes metastases, although it was expressed at very low levels in a few primary tumors. Since it was very close to the significance, we tested LTB expression by IHC. In the second set of validation, LTB immunoreactivity was positive in all tumors cells within the lymph node in all 20 metastases analyzed but was not detected in any adjacent cells (FIG. 2). Additionally, LTB was negative in normal lymph nodes and matched-normal thyroid tissue and primary tumors (FIG. 2). When LTB was investigated by IHC in 15 primary PTC, as suggested by qPCR, 3 out of 15 primary tumors showed a weak staining of LTB in the epithelial tumor cells. LTB was negative in the surrounding normal cells. Interestingly, all positive tumors were highly invasive and had metastasis to the lymph nodes.

In a subsequent study, using another set of matched normal thyroid, normal lymph node, primary tumors and lymph node metastases from the same patient (n=25), IHC analysis was performed for LIMD2, using paraffin-embedded samples. About 90% of the lymph node metastases were positive, and the normal thyroid and normal lymph node were negative.

References
1. Schlumberger M J. Papillary and follicular thyroid carcinoma. N Engl J Med 1998; 338:297-306.
2. Leboulleux S, Rubino C, Baudin E, et al. Prognostic factors for persistent or recurrent disease of papillary thyroid carcinoma with neck lymph node metastases and/or tumor extension beyond the thyroid capsule at initial diagnosis. J Clin Endocrinol Metab 2005; 90:5723-9.
3. Mazzaferri E L, Kloos R T. Clinical review 128: Current approaches to primary therapy for papillary and follicular thyroid cancer. J Clin Endocrinol Metab 2001; 86:1447-63.
4. Sugitani I, Kasai N, Fujimoto Y, Yanagisawa A. A novel classification system for patients with PTC: addition of the new variables of large (3 cm or greater) nodal metastases and reclassification during the follow-up period. Surgery 2004; 135:139-48.
5. Zou M, Famulski K S, Parhar R S, et al. Microarray analysis of metastasis-associated gene expression profiling in a murine model of thyroid carcinoma pulmonary metastasis: identification of S100A4 (Mts1) gene overexpression as a poor prognostic marker for thyroid carcinoma. J Clin Endocrinol Metab 2004; 89:6146-54.
6. Stathatos N, Bourdeau I, Espinosa A V, et al. KiSS-1/G protein-coupled receptor 54 metastasis suppressor pathway increases myocyte-enriched calcineurin interacting protein 1 expression and chronically inhibits calcineurin activity. J Clin Endocrinol Metab 2005; 90:5432-40.
7. Velculescu V E, Zhang L, Vogelstein B, Kinzler K W. Serial analysis of gene expression. Science 1995; 270:484-7.
8. Lal A, Lash A E, Altschul S F, et al. A public database for gene expression in human cancers. Cancer Res. 1999; 59:5403-7.
9. Boon K, Osorio E C, Greenhut S F, et al. An anatomy of normal and malignant gene expression. Proc Natl Acad Sci USA 2002; 99:11287-92.
10. Cerutti J M, Delcelo R, Amadei M J, et al. A preoperative diagnostic test that distinguishes benign from malignant thyroid carcinoma based on gene expression. J Clin Invest 2004; 113:1234-42.

11. Cerutti J M, Latini F R, Nakabashi C, et al. Diagnosis of suspicious thyroid nodules using four protein biomarkers. Clin Cancer Res 2006; 12:3311-8.
12. Radmacher M D, McShane L M, Simon R. A paradigm for class prediction using gene expression profiles. J Comput Biol 2002; 9:505-11.
13. Tukey J W. Tightening the clinical trial. Control Clin Trials 1993; 14:266-85.
14. Simon R, Radmacher M D, Dobbin K, McShane L M. Pitfalls in the use of DNA microarray data for diagnostic and prognostic classification. J Natl Cancer Inst 2003; 95:14-8.
15. Finn S P, Smyth P, Cahill S, et al. Expression microarray analysis of papillary thyroid carcinoma and benign thyroid tissue: emphasis on the follicular variant and potential markers of malignancy. Virchows Arch 2007; 450:249-60.
16. Huang Y, Prasad M, Lemon W J, et al. Gene expression in papillary thyroid carcinoma reveals highly consistent profiles. Proc Natl Acad Sci USA 2001; 98:15044-9.
17. Rosen J, He M, Umbricht C, et al. A six-gene model for differentiating benign from malignant thyroid tumors on the basis of gene expression. Surgery 2005; 138:1050-6; discussion 6-7.
18. Scarpino S, Cancellario d'Alena F, Di Napoli A, et al. Increased expression of Met protein is associated with up-regulation of hypoxia inducible factor-1 (HIF-1) in tumour cells in papillary carcinoma of the thyroid. J Pathol 2004; 202:352-8.
19. Ramirez R, Hsu D, Patel A, et al. Over-expression of hepatocyte growth factor/scatter factor (HGF/SF) and the HGF/SF receptor (cMET) are associated with a high risk of metastasis and recurrence for children and young adults with papillary thyroid carcinoma. Clin Endocrinol (Oxf) 2000; 53:635-44.
20. Beasley N J, Lee J, Eski S, et al. Impact of nodal metastases on prognosis in patients with well-differentiated thyroid cancer. Arch Otolaryngol Head Neck Surg 2002; 128:825-8.
21. Wreesmann V B, Sieczka E M, Socci N D, et al. Genome-wide profiling of papillary thyroid cancer identifies MUC1 as an independent prognostic marker. Cancer Res 2004; 64:3780-9.
22. Cvejic D S, Savin S B, Petrovic I M, et al. Galectin-3 expression in papillary thyroid carcinoma: relation to histomorphologic growth pattern, lymph node metastasis, extrathyroid invasion, and tumor size. Head Neck 2005; 27:1049-55.
23. Inaba M, Sato H, Abe Y, et al. Expression and significance of c-met protein in papillary thyroid carcinoma. Tokai J Exp Clin Med 2002; 27:43-9.
24. Nikiforova M N, Kimura E T, Gandhi M, et al. BRAF mutations in thyroid tumors are restricted to papillary carcinomas and anaplastic or poorly differentiated carcinomas arising from papillary carcinomas. J Clin Endocrinol Metab 2003; 88:5399-404.
25. Namba H, Nakashima M, Hayashi T. et al. Clinical implication of hot spot BRAF mutation, V599E, in papillary thyroid cancers. J Clin Endocrinol Metab 2003; 88:4393-7.
26. Fugazzola L, Mannavola D, Cirello V, et al. BRAF mutations in an Italian cohort of thyroid cancers. Clin Endocrinol (Oxf) 2004; 61:239-43.
27. Trovisco V, Vieira de Castro I, Soares P, et al. BRAF mutations are associated with some histological types of papillary thyroid carcinoma. J Pathol 2004; 202:247-51.
28. Liu R T, Chen Y J, Chou F F, et al. No correlation between BRAFV600E mutation and clinicopathological features of papillary thyroid carcinomas in Taiwan. Clin Endocrinol (Oxf) 2005; 63:461-6.
29. Oler G, Ebina K N, Michaluart P, Jr., Kimura E T, Cerutti J. Investigation of BRAF mutation in a series of papillary thyroid carcinoma and matched-lymph node metastasis reveals a new mutation in metastasis. Clin Endocrinol (Oxf) 2005; 62:509-11.
30. Vasko V, Hu S, Wu G, et al. High prevalence and possible de novo formation of BRAF mutation in metastasized papillary thyroid cancer in lymph nodes. J Clin Endocrinol Metab 2005; 90:5265-9.
31. Bach I. The LIM domain: regulation by association. Mech Dev 2000; 91:5-17.
32. Prendergast G C, Jaffee E M. Cancer immunologists and cancer biologists: why we didn't talk then but need to now. Cancer Res 2007; 67:3500-4.
33. Borrello M G, Alberti L, Fischer A, et al. Induction of a proinflammatory program in normal human thyrocytes by the RET/PTC1 oncogene. Proc Natl Acad Sci USA 2005; 102:14825-30.
34. Fernandis A Z, Cherla R P, Ganju R K. Differential regulation of CXCR4-mediated T-cell chemotaxis and mitogen-activated protein kinase activation by the membrane tyrosine phosphatase, CD45. J Biol Chem 2003; 278:9536-43.
35. Scotton C J, Wilson J L, Milliken D, Stamp G, Balkwill F R. Epithelial cancer cell migration: a role for chemokine receptors? Cancer Res 2001; 61:4961-5.
36. Phillips R J, Burdick M D, Lutz M, et al. The stromal derived factor-1/CXCL12-CXC chemokine receptor 4 biological axis in non-small cell lung cancer metastases. Am J Respir Crit. Care Med 2003; 167:1676-86.
37. Castellone M D, Guarino V, De Falco V, et al. Functional expression of the CXCR4 chemokine receptor is induced by RET/PTC oncogenes and is a common event in human papillary thyroid carcinomas. Oncogene 2004; 23:5958-67.
38. Hehlgans T, Stoelcker B, Stopfer P, et al. Lymphotoxin-beta receptor immune interaction promotes tumor growth by inducing angiogenesis. Cancer Res 2002; 62:4034-40.
39. Lukashev M, Lepage D, Wilson C, et al. Targeting the Lymphotoxin-{beta} Receptor with Agonist Antibodies as a Potential Cancer Therapy. Cancer Res 2006; 66:9617-24.
40. Ringel M D, Balducci-Silano P L, Anderson J S, et al. Quantitative reverse transcription-polymerase chain reaction of circulating thyroglobulin messenger ribonucleic acid for monitoring patients with thyroid carcinoma. J Clin Endocrinol Metab 1999; 84:4037-42.
41. Ditkoff B A, Marvin M R, Yemul S, et al. Detection of circulating thyroid cells in peripheral blood. Surgery 1996; 120:959-64; discussion 64-5.
42. Biscolla R P, Cerutti J M, Maciel R M. Detection of recurrent thyroid cancer by sensitive nested reverse transcription-polymerase chain reaction of thyroglobulin and sodium/iodide symporter messenger ribonucleic acid transcripts in peripheral blood. J Clin Endocrinol Metab 2000; 85:3623-7.
43. Bellantone R, Lombardi C P, Bossola M, et al. Validity of thyroglobulin mRNA assay in peripheral blood of postoperative thyroid carcinoma patients in predicting tumor recurrences varies according to the histologic type: results of a prospective study. Cancer 2001; 92:2273-9.
44. Bugalho M J, Domingues R S, Pinto A C, et al. Detection of thyroglobulin mRNA transcripts in peripheral blood of individuals with and without thyroid glands: evidence for thyroglobulin expression by blood cells. Eur J Endocrinol 2001; 145:409-13.

45. Griffith O L, Melck A, Jones S J, Wiseman S M. Meta-analysis and meta-review of thyroid cancer gene expression profiling studies identifies important diagnostic biomarkers. J Clin Oncol 2006; 24:5043-51.

46. Shi Y, Zou M, Collison K, et al. Ribonucleic acid interference targeting S100A4 (Mts1) suppresses tumor growth and metastasis of anaplastic thyroid carcinoma in a mouse model. J Clin Endocrinol Metab 2006; 91:2373-9.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications (including provisional patent application 60/965,208, filed Aug. 17, 2007) cited above and in the figures are hereby incorporated in their entirety by reference.

TABLE 2

Genes induced in lymph node metastases (LNMs) selected for verification and normal thyroid specific genes.

| Tag sequence | Normal Lymph Node* | Normal Thyroid* | Primary Tumor* | LNMs* | Transcription description† |
|---|---|---|---|---|---|
| GTCAACAGTA (SEQ ID NO: 1) | 0 | 0 | 0 | 21 | ABCC3, ATP-binding cassette, sub-family C (CFTR/MRP), member 3 |
| GCAGTGGGAA (SEQ ID NO: 2) | 0 | 0 | 0 | 38 | LTB, Lymphotoxin beta |
| GTAGCGCCTC (SEQ ID NO: 3) | 0 | 0 | 0 | 9 | CST7, Cystatin F |
| TTAACTGTGT (SEQ ID NO: 4) | 0 | 0 | 0 | 13 | SYT12, Synaptotagmin XII |
| CTTTTTTCCC (SEQ ID NO: 5) | 0 | 3 | 1 | 23 | CD48, B-cell membrane protein |
| TTAAATCCCA (SEQ ID NO: 6) | 2 | 4 | 0 | 29 | PTPRC, Protein tyrosine phosphatase, receptor type C |
| AAAGCAAAAA (SEQ ID NO: 7) | 0 | 4 | 1 | 23 | PTPN4, Protein tyrosine phosphatase, non-receptor type 4 |
| TTTCAATAGA (SEQ ID NO: 8) | 6 | 1 | 1 | 23 | LIMD2 |
| Genes previously associated with papillary metastatic process | | | | | |
| GAGGCCATCC (SEQ ID NO: 9) | 4 | 10 | 1 | 26 | LSM7, U6 small nuclear RNA associated |
| CAATTAAAAT (SEQ ID NO: 10) | 0 | 3 | 25 | 94 | MET proto-oncogene |
| CAGGCCCCAC (SEQ ID NO: 11) | 4 | 17 | 18 | 72 | S100A11, S100 calcium binding protein A11 |
| Genes involved in thyroid function | | | | | |
| GATGAATAAA (SEQ ID NO: 12) | 0 | 75 | 0 | 0 | TPO, thyroid peroxidase |
| CGGTGAAGCA (SEQ ID NO: 13) | 0 | 134 | 16 | 57 | TG, thyroglobulin |
| ATGCTAAGAG (SEQ ID NO: 14) | 0 | 30 | 2 | 0 | DIO2, deiodinase, iodothyronine, type II |

| Tag sequence | Aliases | GenBank Accession no | Location | Gene ontology‡ |
|---|---|---|---|---|
| GTCAACAGTA (SEQ ID NO: 1) | MRP3 | NM_003786 | 17q22 | Transporter activity |
| GCAGTGGGAA (SEQ ID NO: 2) | TNFC | NM_002341 | 6p21.3 | Tumor necrosis factor receptor-binding activity |
| GTAGCGCCTC (SEQ ID NO: 3) | CMAP | BCO15507 | 20p 11.21 | Cysteine protease inhibitor activity |
| TTAACTGTGT (SEQ ID NO: 4) | SRGI | BC037406 | 11q13.2 | Transporter activity |
| CTTTTTTCCC (SEQ ID NO: 5) | BLAST, SLAMF2 | BCO16182 | 1q21 | GPI anchor binding |
| TTAAATCCCA (SEQ ID NO: 6) | LCA, CD45 | NM_002838 | 1q31 | Protein tyrosine phosphate activity |
| AAAGCAAAAA (SEQ ID NO: 7) | PTPMEGI | NM_002830 | 2q14.2 | Protein tyrosine phosphatase activity |
| TTTCAATAGA (SEQ ID NO: 8) | MGC10986 | BC004400 | 17q23.3 | Metal ion binding |
| Genes previously associated with papillary etastatic process | | | | |
| GAGGCCATCC (SEQ ID NO: 9) | No | BC018621 | 19p13.3 | RNA binding |

TABLE 2-continued

Genes induced in lymph node metastases (LNMs) selected for verification and normal thyroid specific genes.

| | | | | |
|---|---|---|---|---|
| CAATTAAAAT (SEQ ID NO: 10) | HGFR, RCCP2 | NM_000245.2 | 7q3 I | Protein tyrosine-kinase active |
| CAGGCCCCAC (SEQ ID NO: 11) | Calgizzarin | B0001410 | Iq21 | Calcium ion binding |
| Genes involved in thyroid function | | | | |
| GATGAATAAA (SEQ ID NO: 12) | No | M17755 | 2p25 | Thyroid hormone generation |
| CGGTGAAGCA (SEQ ID NO: 13) | No | NM_003235 | 8q24.2 | Thyroid hormone generation |
| ATGCTAAGAG (SEQ ID NO: 14) | No | NM_000793 | 14q24.2 | Thyroid hormone generation |

NOTE:
SAGE libraries are posted at http://cgap.nci.nih.gov/SAGE.
*SAGE tags counts shown in each column refer to the abundance of SAGE tags in the libraries after normalization to 200,000 total tags.
†Transcript description refers to the gene name to which tag was attributed, according to the HUGO/GDB nomenclature committee approved symbols.
‡Gene classification was by molecular function (http://cgap.nci.nih.gov/Genes/AllAboutGO)

We claim:

1. A method for detecting the presence of lymph node metastases in a subject having papillary thyroid carcinoma (PTC), comprising
    measuring in a sample from the subject the amount of expression of one or more of the following proteins, compared to a baseline value:
    (a) LIMD2, and/or
    (b) LTB,
    wherein a significant amount of over-expression of the protein(s) compared to the baseline value indicates that lymph node metastases are likely to be present in the subject.

2. The method of claim 1, wherein the amount of expression of both of the proteins is measured.

3. The method of claim 1, further comprising measuring the amount of expression of
    (c) PTPRC, and/or
    (d) CD48, and/or
    (e) ABCC3,
    wherein a significant amount of over-expression of protein(s) (c), (d) and/or (e) compared to the baseline value further indicates that lymph node metastases are likely to be present in the subject.

4. The method of claim 3, wherein the amount of expression of at least four of the proteins is measured.

5. The method of claim 3, wherein the amount of expression of all five of the proteins is measured.

6. The method of claim 1, wherein the sample is from a lymph node biopsy.

7. The method of claim 1, wherein the sample is from serum.

8. The method of claim 7, further comprising measuring the amount of expression of serum thyroglobulin (TG), wherein a significant amount of over-expression of TG compared to the baseline value further indicates that lymph node metastases are likely to be present in the subject.

9. The method of claim 1, wherein the amount of expression of a protein is determined by measuring the amount of mRNA encoding the protein.

10. The method of claim 9, wherein the measuring of the amount of an mRNA is accomplished by a method comprising hybridizing the mRNA to a probe that is specific for the mRNA, under conditions that are effective for specific hybridization of the mRNA to the probe.

11. The method of claim 1, wherein the amount of expression of a protein is determined by measuring the amount of the protein.

12. The method of claim 11, wherein the measuring of the amount of a protein is accomplished by a method comprising binding the protein to an antibody that is specific for the protein, under conditions effective for specific binding of the protein to the antibody.

13. The method of claim 12, wherein the antibody is contacted with a histological preparation of a biopsy sample from a lymph node, and is visualized by immunohistochemical staining.

14. The method of claim 1, further comprising,
    if the subject is determined to be likely to have lymph node metastases, treating the subject aggressively for the PTC, and
    if the subject is determined not to be likely to have lymph node metastases, not treating the subject aggressively for the PTC.

15. The method of claim 1, which is a method for following the progression of the PTC.

16. The method of claim 1, wherein the detection is carried out both before or at approximately the same time as, and after, the administration of a treatment, and which is a method for determining the effectiveness of the treatment.

17. The method of claim 1, which is a method for determining recurrence of PTC.

18. The method of claim 1, wherein the subject is human.

* * * * *